United States Patent [19]

Anshus et al.

[11] 4,187,370

[45] Feb. 5, 1980

[54] POLYMERIZATION AND RECOVERY OF 2-PYRROLIDONE WITH ACID TREATMENT

[75] Inventors: Byron E. Anshus, Orinda; Kiyoshi Katsumoto, El Cerrito; Ira M. Serkes, Berkeley, all of Calif.

[73] Assignee: Chevron Research Company, San Francisco, Calif.

[21] Appl. No.: 842,758

[22] Filed: Oct. 17, 1977

Related U.S. Application Data

[63] Continuation-in-part of Ser. No. 792,421, Apr. 29, 1977, Pat. No. 4,139,696.

[51] Int. Cl.² ............................................. C08G 69/24
[52] U.S. Cl. .................................. 528/312; 528/326; 528/486; 528/487; 528/490
[58] Field of Search ............... 528/312, 326, 486, 487, 528/490

[56] References Cited

U.S. PATENT DOCUMENTS

| | | | |
|---|---|---|---|
| 3,184,476 | 5/1965 | Wingfield et al. | 260/326.5 FL |
| 3,213,066 | 10/1965 | Renfrew | 528/312 |
| 3,681,293 | 8/1972 | Jarovitzky et al. | 528/312 |
| 3,778,402 | 12/1973 | Kimura et al. | 528/312 |
| 3,968,087 | 7/1976 | Choi | 528/312 |
| 4,050,994 | 9/1977 | Anshus | 528/312 |

*Primary Examiner*—Harold D. Anderson
*Attorney, Agent, or Firm*—D. A. Newell; T. G. DeJonghe; L. S. Squires

[57] ABSTRACT

An alkaline-catalyzed process for preparing poly-2-pyrrolidone characterized by the step of treating the polypyrrolidone reaction product mixture with an acid to prevent polymer agglomeration and prevent base-catalyzed polymer degradation. In another embodiment, unreacted poly-2-pyrrolidone is recovered by washing the acid-treated polymer reaction product mixture with water and the resulting wash water recovered, treated with further acid, and then subjected to a two-stage evaporation process. Poly-2-pyrrolidone is known as nylon 4, and can be shaped into filaments and various molded articles.

12 Claims, No Drawings

POLYMERIZATION AND RECOVERY OF 2-PYRROLIDONE WITH ACID TREATMENT

CROSS-REFERENCE TO RELATED APPLICATIONS

This application is a continuation-in-part of application Ser. No. 792,421, filed Apr. 29, 1977, now U.S. Pat. No. 4,139,696, the disclosure of which is incorporated herein by reference.

BACKGROUND OF THE INVENTION

1. Field of the Invention

This invention relates to an alkaline-catalyzed process for polymerizing 2-pyrrolidone. In a further aspect, this invention relates to such an alkaline-catalyzed process wherein the reaction product mixture of particulate poly-2-pyrrolidone is treated with acid to reduce the pH of the mixture. In another aspect, this invention relates to a process for the recovery of unreacted 2-pyrrolidone from the afore-described polymerization processes.

2. The Prior Art

Poly-2-pyrrolidone (or nylon 4) is produced by the alkaline-catalyzed polymerization of 2-pyrrolidone.

Polypyrrolidone is generally produced by the batch bulk polymerization. The monomer and catalysts were charged to a reactor and held at polymerization temperature for 20 or more hours to obtain a hard block of polymer. Since, in general, only 30–70% of the monomer was converted to polymer, the product had to be chopped, ground and extracted with water to recover unreacted monomer. The final polymer particle size depended on the extent of grinding, as well as the percent conversion to polymer. Polymerization under agitation, such as in a stirred reactor, produces a product which is a powder or alkaline paste or slurry of particulate polypyrrolidone and polymerizate. At conversions above about 40 percent, the product is powdery. The product is conveniently washed with water to provide a particulate polypyrrolidone without grinding. However, a considerable amount of polymer degradation occurs if the alkaline product is contacted with water while still at the elevated temperature of the polymerization reactor. If, on the other hand, the alkaline product is allowed to stand before contacting with water, it becomes a hard block of polymer requiring the same processing as the batch bulk polymerization product. In our copending U.S. application Ser. No. 792,421, we described an improved continuous process which included a unique acid treatment which eliminated these problems. The present invention is concerned with the broad application of this treatment to substantially eliminate these problems, in both continuous and batch processes.

In polymerizing 2-pyrrolidone using an alkaline catalyst, the recovery of unreacted pyrrolidone has been accomplished by the prior art by several methods all of which begin by washing the incompletely reacted polymerizate with water or a water-miscible solvent to extract the alkaline catalyst and unreacted pyrrolidone. In commonly assigned U.S. application Ser. No. 745,501, filed Nov. 26, 1976, now U.S. Pat. No. 4,050,994 an improved process is described for recovering pyrrolidone from the resulting wash waters. The process, described therein, comprises treating the alkaline wash water with acid followed by a two-stage evaporation. We have found that even though the pre-washed polymerization reaction product slurry is treated with acid in our process, and hence the resulting wash waters may already be neutral or even slightly acidic, the application of acid to such waters facilitates more efficient recovery of 2-pyrrolidone. Various pyrrolidone recovery processes are illustrated by U.S. Pat. Nos. 3,681,1293 and 3,290,329.

SUMMARY OF THE INVENTION

In summary, one process of the invention comprises polymerizing 2-pyrrolidone in the presence of an alkaline catalyst and treating the poly-2-pyrrolidone reaction product mixture with acid to reduce its pH to about from 5–8. In summary, a further embodiment of this process comprises washing the so-treated product mixture with water and recovering the pyrrolidone-alkaline catalyst water-wash solution and treating the recovered wash solution with acid followed by two-stage evaporation to recover the pyrrolidone therefrom.

FURTHER DESCRIPTION OF THE INVENTION

In its broadest aspect the process of the invention for preventing base-catalyst polymer degradation and polymer agglomeration is broadly applicable to virtually any alkaline-catalyzed process for polymerizing pyrrolidone. Thus, the polymerization can be conveniently effected by polymerizing a mixture of pyrrolidone monomer, alkaline lactamate (catalyst), and optional activators and accelerators, in a suitable organic solvent. Typically, and preferably, an excess of pyrrolidone is used as the solvent; however, other inert organic solvents such as paraffinic hydrocarbons, such as hexane, heptane, and the like, could also be used. Also, as is well recognized, the polymerization is preferably conducted under anhydrous or substantially anhydrous conditions; i.e., the reaction mixture should contain less than about 0.2% water, based on the weight of pyrrolidone and solvent, and preferably less than about 0.05%. The optimum catalyst pyrrolidone ratio and polymerization temperatures will vary with the particular catalyst system used; however, typically polymerization temperatures and polymerization times in the range of about from 15° to 100° C., preferably 25° C. to 70° C., and of about from 4 to 100 hours preferably about from 6 to 72 hours, are used. Generally, best results are obtained using polymerization temperatures in the range from about 40° C. to 80° C. and polymerizaton times of about from 6 to 48 hours. In a typical alkali metal pyrrolidonate catalyst system, using pyrrolidone as the solvent, a catalyst content of about from 0.5 to 30 mol percent, preferably about from 1 to 20 mol percent based on total pyrrolidone, is used. Typically, best results are obtained using about 10 mol percent catalyst, based on total pyrrolidone. "Total pyrrolidone" refers to all of the pyrrolidone charged to the system, including that present in the catalyst as well as solvent and reactant.

In accordance with the practice of the present invention, the polymer reaction product mixture (e.g., a slurry, viscous paste, or powder, of poly-2-pyrrolidone, alkaline catalyst and solvent) is treated with sufficient acid to form a mixture having a pH of about from 5 to 8. Typically, the acid treatment is conducted at temperatures in the range of about from 20° to 70° C. and preferably about from 30° to 60° C. In order to be effective to prevent polymer agglomeration, the acid treatment should, of course, be effected before the polymer agglomerates and hardens. Preferably, the reaction product mixture is discharged into another vessel for the acid treatment in order to facilitate continuous use of the reactor. Polymer agglomeration is particularly undesirable, since the hardened polymer mass can only be removed from the reactor or discharge vessel with extreme difficulty, and if the hardening occurs in the reaction product conveying equipment (typically conveyor augers or screws), this results in the jamming or breakdown of this equipment.

The particular acid used is not critical, so long as it does not cause undue contamination problems or unusual polymer degradation problems in the treatment. Both inorganic and organic acids can be used. Suitable organic acids which can be used include, for example, strong organic acids such as acetic acid, propionic acid, formic acid, p-toluenesulfonic acid, and the like, and mixtures thereof. Preferably, strong mineral acids such as, for example, sulfuric acid, hydrochloric acid, phosphoric acid, and the like or mixtures thereof are used. Conveniently, an aqueous solution of the acid is used. Also water can be added with or immediately prior to the addition of the acid to facilitate dispersion of the acid or at any time after the polymerization in order to facilitate material handling and transportation of the reaction product mixture.

As before-noted, the amount of acid used should be adjusted to reduce the pH of the reaction product mixture such that the resulting slurry has a ph in the range of about from 5 to 8. This is important, since lower pH's can cause acid degradation of the polymer and higher pH's are ineffective to prevent base degradation of the polymer. The acid treatment also prevents base-catalyzed polymer degradation (hydrolysis), and consequently permits washing with water at temperatures up to about 70°–80° C.

As noted before, the acid treatment also prevents polymer agglomeration and is especially applicable to continuous polymerization processes. Where a continuous system is used, it is especially preferred to transfer the product reaction mixture from the reactor or polymerization zone to another vessel or zone, maintained at about the same temperature as the polymerization zone, and contact the reaction product mixture with the acid in this vessel or zone as a separate operation or step in the continuous process sequence. The resulting mixture from this step is then conveniently transferred to a countercurrent (water) washer to remove solvent, salts and other soluble impurities.

For purposes of illustration, a preferred, non-limiting embodiment of the invention, illustrating a continuous process for the polymerization of 2-pyrrolidone, will be described. An aqueous hydroxide, such a 40% by weight aqueous potassium hydroxide, is mixed with an excess of distilled pyrrolidone to form an alkaline mixture which is subjected to a rapid dehydration. Rapid dehydration can be accomplished for example, by flash evaporation, such as in a thin-film evaporator. The dehydrated product is a substantially anhydrous solution of a pyrrolidonate salt, such as potassium 2-pyrrolidonate, in 2-pyrrolidone. The 2-pyrrolidonate salt is a polymerization catalyst. This solution is then sent to a carbonator, or the polymerization vessel, where carbon dioxide is added to the solution to form a carbonated alkaline mixture which is then held under polymerization conditions. Rapid dehydration of the alkaline mixture was favored to avoid the base-catalyzed hydrolysis of 2-pyrrolidone to 4-aminobutyric acid which interfered with carbonation and thereby reduced the amount of carbonated catalysts available. If carbonation is substantially effected, then the yield of high-molecular-weight poly-2-pyrrolidone is greatly reduced. However, we also discovered that dimer was destroyed (hydrolyzed) by heating in the presence of base and that less dimer is destroyed by such rapid dehydration than by longer dehydration. Hence, it was necessary to balance the need to hydrolyze pyrrolinyl-pyrrolidone (dimer) against the danger of hydrolyzing the sensitive 2-pyrrolidone ring.

The dimer is a problem, because in order to achieve the high conversion of 2-pyrrolidone to polymer of high molecular weight, it is very desirable to maintain a close control of the nature and amount of polymerization initiators and polymerization catalysts present in the polymerizate. Because each molecule of initiator is theoretically capable of giving rise to one polymer molecule, it is hypothesized that an overabundance of initiator molecules produces a high conversion of monomer to polymer of low molecular weight in a short time. This is evidenced in a continuous polymerization process by line plugging or build-up of low-molecular-weight solid polypyrrolidone. For example, the presence of 0.6 weight percent of pyrrolinyl-pyrrolidone in the monomer feed was found to produce excessive line plugging by premature polymerization. This problem is not encountered when catalyst is prepared by batch dehydration of the pyrrolidone-KOH solution because the longer dehydration time required in batch polymerization destroys the pyrrolinyl-pyrrolidone polymerization initiator. The continuous process, with its short contact time between the addition of aqueous hydroxide and the charging of the polymerizate to the reactor was found to present the unexpected risk of a runaway polymerization because the amount of dimer was not sufficiently reduced. On the other hand, the optimum selection of the amount of a seleced initiator produces a high conversion of monomer to polymer of high molecular weight in a reasonable period of time. It is found that such an initiated continuous polymerization can be achieved by optimization of the amount of pyrrolinyl-pyrrolidone in the polymerizate by continuously subjecting the alkaline mixture of aqueous hydroxide and 2-pyrrolidone to a brief heat treatment, i.e., a step achieving hydrolysis of the dimer.

Typically, in the preferred operation of this process, the initial commercial pyrrolidone is purified for polymerization by fractional distillation. The middle fraction is taken, but may still contain as much as several percent pyrrolinyl-pyrrolidone, typically about 1 weight percent pyrrolinyl-pyrrolidone. This amount of dimer is both exceedingly difficult to remove and very deleterious to the continuous polymerization process.

Hence, in a typical process of this embodiment, the middle fraction of 2-pyrrolidone is used for in-situ catalyst production by contacting same with an aqueous hydroxide solution. The aqueous hydroxide solution can be a solution of an alkaline metal hydroxide, an alkaline earth metal hydroxide, or a quaternary ammonium hydroxide. Preferably, it is an alkali metal hydroxide such as aqueous NaOH or preferably aqueous KOH, having a concentration of 10–60 weight percent hydroxide. An aqueous NaOH solution of about 10–25 weight percent NaOH is also preferred, but most satisfactory results have heretofore been obtained with aqueous KOH solutions of 20–60 weight percent, and usually of 35–45 weight percent KOH. (See U.S. Pat. No. 3,778,402). The aqueous hydroxide is continuously contacted with the distilled 2-pyrrolidone in relative amounts such that an excess of 2-pyrrolidone is present. The hydroxide and 2-pyrrolidone are normally fed at a rate such that hydroxide constitutes 0.5–30 mol percent, preferably about 5–20 mol percent, and most preferably about 10 mol percent of the mixture, based on total 2-pyrrolidone. That is, after dehydration, the amount of catalysts, i.e. the amount of 2-pyrrolidonate salts, constitutes 0.5–30 mol percent, preferably about 5–20 mol percent, and most preferably about 10 mol percent of the dehydrated mixture based on total 2-pyrrolidone. Total 2-pyrrolidone includes both 2-pyrrolidone and 2-pyrrolidonate salt.

In order to reduce the dimer content of the alkaline mixture within the desired limits by hydrolysis of the dimer, the alkaline mixture of aqueous hydroxide and 2-pyrrolidone is maintained at a temperature of about 25°–60° C., preferably 30°–50° C., for a period of about 3–60 minutes, preferably about 10–60 minutes, at a pressure ranging from subatmospheric to superatmospheric, preferably at atmospheric pressure. The time period of hydrolysis which is selected can be varied inversely to the temperature of hydrolysis which is selected, and vice versa, to achieve hydrolysis of the dimer to within the desired limits. The hydrolysis zone can simply consist of an isolated and thermostated vessel whose volume is chosen to give a residence time corresponding to the selected period of hydrolysis under the chosen conditions of continuous feeding of the alkaline mixture and temperature. Depending on the dimer content of the distilled monomer, the alkaline mixture may enter the hydrolysis zone containing appreciable pyrrolinyl-pyrrolidone, but will exit from this zone after the selected period of hydrolysis, containing about 0.01–0.1 weight percent dimer and preferably containing less than 0.05 weight percent dimer, based on the weight of total 2-pyrrolidone (the weight of total 2-pyrrolidone includes the weight of 2-pyrrolidone and the 2-pyrrolidone component of the catalyst salt.)

The alkaline mixture, containing only the desired amount of dimer, is sent to the dehydration zone consisting, for example, of a thin-film evaporator, or a vacuum distillation column, where water is rapidly removed under conditions which provide a dehydrated mixture, containing less than about 1000 ppm water, preferably less than 500 ppm water, based on the weight of total 2-pyrrolidone. Preferably the mixture is dehydrated under reduced pressure, preferably at 2–100 mm, and most preferably at 2–10 mm and about 75°–190° C. The dehydrated alkaline mixture of 2-pyrrolidonate salt and 2-pyrrolidone is then sent to the carbonation zone, preferably being transferred through heated lines which maintain a temperature of about 70°–90° C. in order to retard polymerization. To the substantially anhydrous mixture containing less than about 1000 ppm water, is added carbon dioxide, preferably while said dehydrated alkaline mixture is maintained at a temperature of about 60°–95° C., preferably 70°–90° C. Sufficient carbon dioxide is absorbed by the alkaline mixture by provision of contact area and contact time such that carbon dioxide is added to the extent of about 10–50 mol percent based on the hydroxide, thus at 10 mol percent hydroxide, carbon dioxide is added to the extent of about 1–5 mol percent based on total 2-pyrrolidone. Preferably, carbon dioxide constitutes about 1–5 mol percent, most preferably about 3 mol percent of the alkaline mixture based on total 2-pyrrolidone. The carbonated alkaline mixture is sent to the polymerization zone where it is preferably mixed with additional purified monomer and additional polymerization promoters such as N-acyl compounds, tetramethylammonium halide, sulfur dioxide, acetic acid anhydride, dimer, etc.

Dimer, present in the purified monomer in known amount, is conveniently added to the polymerizate in controlled amounts by this means to initiate polymerization. Preferably, about 0.08–0.15 weight percent dimer, based on total 2-pyrrolidone including the added monomer, is added to the polymerizate by means of the addition of purified monomer.

The polymerization zone consists of one or more reactors, preferably used in series, wherein the temperature is maintained at 20°–90° C., preferably about 40°–60° C. and most preferably about 45°–55° C., and wherein the polymerization is subjected to continual agitation, such as is provided by a stirred reactor mechanism. In continuous operation, the number of pounds of polymerizate in the reactor, divided by the feed rate of polymerizate in pounds/hour (which is substantially identical to the product take-off rate in continuous operation) equals the residence time in the polymerization reactor. The residence time, i.e. the reactor volume and the feed rate, is selected to provide product polymer of the desired molecular weight and to provide the desired degree of conversion of monomer to polymer. Generally, residence times are 4–36 hours, preferably 6–24 hours, depending on the temperature, the product desired, and the amounts of initiator and catalysts used to achieve that product.

The polymer exits the polymerization zone and is subjected to washing, drying, pelletization, etc. as may be necessary for its ultimate use. Under these continuous polymerization conditions, the agitated reactor holds a product which is a powder, paste or slurry consisting of particulate poly-2-pyrrolidone in the polymerizate, i.e. in the carbonated alkaline mixture continuously provided. Preferably, the reactor holds a powder which can then be withdrawn from the polymerization zone by an auger-like take-off or as a continuous overflow discharge at a constant rate. The product from the reactor is then treated with acid, as described above, preferably while maintaining the product at about polymerization zone temperature, and before substantial cooling of the product to a hard mass is allowed to occur.

The polymerization processes or treatments of the present invention are generally applicable to the production of polymers of C-alkyl-substituted pyrrolidone, such as 4-methyl-2-pyrrolidone, and to the production of copolymers of 2-pyrrolidone, such as pyrrolidone/caprolactam copolymers as to the production of poly-2-pyrrolidone. Thus, in general, the processes will find use in the polymerization of 2-pyrrolidone, substituted 2-pyrrolidone, and any monomer capable of copolymerizing with 2-pyrrolidone under the stated conditions of alkaline polymerization catalysis. Preparation of polymers of 2-pyrrolidone using the process of this invention can be carried out with various amounts of monomer, catalysts, inert non-solvent liquids as in a dispersion polymerization, initiators, activators and other additives—the amount of each being properly coordinated to produce the most effective polymerization. Such polymerization initiators and catalysis aids include N-acyl lactams such as N-acetyl pyrrolidone or equivalently compounds such as acetic anhydride. Sulfur dioxide may be usable as a partial substitute for carbon dioxide and tetraalkyl ammonium halides such as tetramethyl ammonium chloride may find use in the polymerizate.

A detailed description of a further exemplification of a continuous polymerization process is set forth on page 11, line 5, through page 12, line 16, of the above-referenced parent application U.S. Ser. No. 792,421, which description is hereby incorporated by reference.

It is, of course, desirable to recover, and reuse, unreacted pyrrolidone from the product reaction mixture. Accordingly, after the acid treatment described above, the product reaction mixture is washed with water, in accordance with the present invention, at temperatures in the range of about from 60° to 80° C., preferably about 65° to 75° C., to remove pyrrolidone, salts, and other soluble impurities. This can be effected either via a batch process, for example direct washing in the reactor or discharge vessel, or preferably in the case of a continuous operation by transferring the reaction product mixture to a countercurrent extractor. Typically, such wash solutions contain about 10-50 weight percent 2-pyrrolidone and because of the acid treatment have a pH of about 5 to 8 as compared to pH's of about 12 to 13, which are generally obtained by the prior art processes. In accordance with the present invention, relatively pure 2-pyrrolidone is recovered by treating the wash solution with an acid, such as sulfuric acid, to lower the pH to about 7 or lower, and preferably about 3 to 5, i.e., a neutral or preferably acidic, solution. The particular acid used is not critical so long as it yields a salt with the alkaline catalyst which, in of itself, does not present unusual purification problems. Good results are obtained using strong mineral acids such as sulfuric acid, hydrochloric acid, phosphoric acid, and the like, or mixtures thereof, and especially sulfuric acid. Suitable organic acid which can be used also include, for example, strong organic acids such as acetic acid, propionic acid, formic acid, p-toluenesulfonic acid, and the like, and mixtures thereof. Preferably and conveniently, aqueous acid solutions are used.

The neutralized or acidified solution is then subjected to a first rapid evaporation, of the order of minutes to at most a few hours at atmospheric, but preferably under reduced pressure, preferably at about 25-100 mm Hg (torr). The first evaporation removes a major amount, preferably about 90 weight percent or more, of the water present in the neutralized solution, and most preferably about 98-99%. This first evaporation is preferably carried out at temperatures of about 50°-100° C., but in general less than about 120° C. Preferably a forced circulation evaporator is used.

The evaporation of this large quantity of water typically precipitates a substantial amount of solids, e.g., salts such as potassium sulfate, which are relatively insoluble in 2-pyrrolidone. Where the salts are soluble in pyrrolidone, they are removed in the second evaporation step. Thus the product of the first evaporative step is normally a slurry of salts in 2-pyrrolidone and water. Furthermore, unless the evaporation is carried out substantially under these conditions, an appreciable amount, i.e. as much as 5 percent or more, of a benzene-insoluble organic residue is produced which effectively prevents the complete recovery of 2-pyrrolidone from the slurry in later steps of the process. The unsatisfactory slurry is observed to be "pasty". The residue is believed to comprise an oligomer or derivative of 2-pyrrolidone, such as gamma-amino-butyric acid.

The entire slurry, or the filtrate from the slurry, is directly subjected to a second evaporation at reduced pressure, i.e., most preferably about 3-5 torr, but preferably less than about 10 torr. The temperature of the slurry during the evaporative process is not critical, but is preferably about 100°-150° C. and most preferably about 110° C. The vaporization is carried out until the solid residue is substantially dry. The second evaporation is preferably carried out in a thin-film dryer having at least about 3 square feet of evaporator surface per 100 pounds/hour of overhead. Alternatively, the solids can be removed from the slurry prior to the second evaporation, for example by centrifugation or filtration.

This process results in the recovery of more than 95% of the 2-pyrrolidone originally present in the dilute alkaline aqueous wash water, less than about 1-2% being lost as benzene-insoluble residue on the solid salt residue. The recovered 2-pyrrolidone is of such high purity that it may be directly polymerized or preferably mixed with fresh 2-pyrrolidone for the normal preliminary purification prior to the making of polymerization catalysts. This purification is normally carried out by distillation.

This process has the additional advantage in that it has been found to destroy certain of the deleterious impurities which occur in 2-pyrrolidone, namely, and principally, butanediol. Butanediol is the major polymerization inhibitor round in 2-pyrrolidone made by certain procedures. It is not consumed in the polymerization reaction, so that continual recycling of unreacted 2-pyrrolidone would lead to the build-up of butanediol to an unacceptable level and eventual poisoning of the polymerization. The present process using, for example, sulfuric acid and acidified solutions of pH 3-5, carried out in repeated recycling of excess 2-pyrrolidone in incomplete polymerizations, results in a very limited build-up of butanediol to only about 0.02 mol percent based on total 2-pyrrolidone at each stage of repeated polymerization. Acidification of the alkaline aqueous solutions tends to destroy butanediol. Other impurities which occur in 2-pyrrolidone can be essentially eliminated, if necessary, by bleeding a 2-5% side-stream from the recycled 2-pyrrolidone and either discarding it or purifying it.

The pyrrolidone recovery step can comprise additional steps and treatments as are deemed felicitous for the treatment of crude pyrrolidone. For example, the 2-pyrrolidone vaporized from the slurry may be subjected to condensation in a partial condenser to achieve an extra stage of separation. 2-Pyrrolidone can also be purified by recrystallization from water solutions.

In the afore-described pyrrolidone polymerization and recovery processes and treatments, where typical or preferred conditions (e.g., temperatures, mol ratios, reaction time, etc.) have been given, it should be appreciated that other conditions both above and below these ranges can also be used, though generally with poor results or econonics.

A further understanding of the invention can be had from the following non-limiting exemplifications, wherein Example 1 is a calculated example illustrating a continuous polymerization process species of the present invention, Example 2 is a calculated example illustrating a batch process of the invention, and Examples 3 and 4 are calculated examples illustrating the recovery of pyrrolidone from the wash solutions of Examples 3 and 4, respectively.

EXAMPLE 1

Two thousand pounds/hr of freshly distilled 2-pyrrolidone is charged through a line mixer simultaneously with 330 pounds/hr of a 40% aqueous potassium hydroxide solution. The alkaline mixture is then transferred at 2330 pounds/hr to a vessel maintained at 40° C. After an average residence time of 15 minutes, the heat-treated alkaline mixture is passed into a distillation zone comprising a wiped-film evaporator maintained at 80° C. and 3 mm pressure, and wherein 240 pounds/hr of water is vaporized and removed from the alkaline mixture. The dehydrated alkaline mixture at 80° C. is next passed at 2090 pounds/hr into a carbonation vessel wherein it reacts with 31 pounds/hr of carbon dioxide. The resultant carbonated alkaline mixture is maintained at 80° C. while passing from the carbonation vessel to the polymerization reactor. The polymerization reactor is a stirred, conical vessel in which about 16,000 pounds of polymerizate is continuously mixed at 50° C. The polymerization vessel contains a heavy paste of particulate polypyrrolidone and liquid polymerizate which is removed by means of an auger, and with essentially no cooling is charged to the neutralization vessel at 2121 pounds/hr after an average polymerization time of 6–8 hours. The neutralizer is concurrently provided with 120 pounds/hr of concentrated 98% aqueous sulfuric acid and 1000 pounds/hr of a water-pyrrolidone-$K_2SO_4$ solution from the countercurrent washer. The resulting slurry is stirred at a temperature of 50° C. for an average of 10 minutes. Overflow from the neutralizer next passes at 3241 pounds/hr into a water washer wherein it is contacted countercurrently by 5000 pounds/hr of water at 50° C. The used wash water, containing 1000 pounds/hr of pyrrolidone, is sent to monomer recovery facilities. The washed polymer, 1500 pounds/hr, is dried by heating at 120° C. under atmospheric pressure in a fluidized dryer for 30 minutes. In this way, there is obtained 1000 pounds/hr of dry, polypyrrolidone powder having a weight average molecular weight of about 300,000.

EXAMPLE 2

This example illustrates a batch process for the polymerization of pyrrolidone according to the invention.

In this example, 200 pounds (2.35 lb-mols) of purified 2-pyrrolidone is placed in a reactor equipped for vacuum distillation and fitted with a gas inlet tube. 15.4 lbs (0.235 lb-mol, 10 mol percent based on 2-pyrrolidone) of 85.7% pure anhydrous potassium hydroxide is added and the reactor then swept with gaseous nitrogen. The mixture is then placed under reduced pressure and heated to incipient distillation of pyrrolidone to remove water formed by the reaction of pyrrolidone and potassium hydroxide. The resulting solution is then cooled to 30° C. and 3.1 lbs (0.07 lb-mol, 3 mol percent based on total pyrrolidone) of carbon dioxide is bubbled through the solution, under vacuum. The flask is then brought to atmospheric pressure by the addition of dry gaseous nitrogen. The mixture is heated and maintained at 50° C., with stirring, for 12 hours and then transferred to another vessel. Aqueous 2% sulfuric acid (700 lbs) is then metered into the product reaction mixture with stirring, until pH-sensing instruments in the vessel indicate that the pH of the reaction product slurry is reduced to pH 7. The slurry is then centrifuged to recover the relatively high-molecular-weight poly-2-pyrrolidone solids.

EXAMPLE 3

This example illustrates the recovery of pyrrolidone from the wash-water solution of Example 1. 8000 lbs. of wash-water solution from Example 1 containing 12.5 weight percent 2-pyrrolidone (1000 lbs) is neutralized to pH 4 with concentrated 98% sulfuric acid. Water is removed from the acidified solution by evaporation at 50°–110° C. and 50-100 torr over a 13-hour period to produce a slurry containing about 80 weight percent organic material (including 2-pyrrolidone), 20 weight percent $K_2SO_4$ and less than 1 weight percent water. The slurry is then fed into a heated thin-film drier at 5 torr, affording a dry potassium sulfate bottoms producing containing 2% organic residue and a polymerizable 2-pyrrolidone overhead product.

EXAMPLE 4

This example illustrates the recovery of pyrrolidone from the solution recovered from the centrifuge of Example 2. 700 lbs of wash-water solution from Example 2 containing about 14 weight percent 2-pyrrolidone (100 lbs) is neutralized to pH 5 with concentrated 98% aqueous sulfuric acid. Water is removed from the acidified solution by evaporation at 50°–110° C. and 50-100 torr over a 13-hour period to produce a slurry containing about 80 weight percent organic material (including 2-pyrrolidone), 20 weight percent $K_2SO_4$ and less than 1 weight percent water. The slurry is then fed into a heated thin-film drier at 5 torr, affording a dry potassium sulfate bottoms product containing 2% organic residue and a polymerizable 2-pyrrolidone overhead product.

Obviously, many modifications and variations of the invention, described hereinabove and below in the claims, can be made without departing from the essence and scope thereof.

What is claimed is:

1. A process for the polymerization of pyrrolidone, which comprises polymerizing under substantially anhydrous conditions a mixture containing alkaline catalyst, pyrrolidone, and solvent, to form a substantially anhydrous reaction product mixture consisting essentially of particulate poly-2-pyrrolidone, alkaline catalyst and solvent and, before said poly-2-pyrrolidone can appreciably agglomerate, treating said reaction product mixture with an acid to reduce the pH of the resulting mixture to about from 5 to 8.

2. The process of claim 1 wherein said acid is an aqueous acid.

3. The process of claim 1 wherein said acid is a strong mineral acid or a strong organic acid.

4. The process of claim 3 wherein said acid is selected from the group consisting of sulfuric acid, hydrochloric acid, phosphoric acid, and mixtures thereof.

5. The process of claim 4 wherein said acid is sulfuric acid.

6. The process of claim 1 wherein said solvent is pyrrolidone.

7. The process of claim 6 wherein said acid is sulfuric acid.

8. The process of claim 1 wherein the treatment of said reaction product mixture with said acid is effected at temperatures in the range of about from 20° to 70° C.

9. The process of claim 1 wherein said alkaline catalyst is prepared by reacting an excess of pyrrolidone with an alkali metal hydroxide to yield a solution of an alkali metal salt of pyrrolidone in pyrrolidone.

10. The process for the polymerization of 2-pyrrolidone according to claim 9, wherein said alkali metal hydroxide is an aqueous alkali metal hydroxide solution.

11. The process for the polymerization of 2-pyrrolidone according to claim 10, wherein said alkali metal hydroxide solution is a potassium hydroxide solution containing 20-60 weight percent KOH.

12. The process of claim 9, wherein said alkali metal salt of pyrrolidone solution is dehydrated to substantially remove water and is then contacted with carbon dioxide at a temperature of about 60°-95° C. to provide a carbonated alkaline mixture containing about 1-5 mol percent carbon dioxide based on total 2-pyrrolidone and polymerizing the resulting mixture at a temperature in the range of about 40°-60° C.

* * * * *